(12) United States Patent
Hwang et al.

(10) Patent No.: US 10,058,570 B2
(45) Date of Patent: Aug. 28, 2018

(54) USE OF ARSENIC COMPOUNDS FOR TREATMENT OF PAIN AND INFLAMMATION

(71) Applicant: Panaphix Inc., Closter, NJ (US)

(72) Inventors: Michael Hwang, Chappaqua, NY (US); Yong Jin Yang, Kyonggi-do (KR)

(73) Assignee: Panaphix Inc., Closter, NJ (US)

( * ) Notice: Subject to any disclaimer, the term of this patent is extended or adjusted under 35 U.S.C. 154(b) by 1112 days.

(21) Appl. No.: 13/869,911

(22) Filed: Apr. 24, 2013

(65) Prior Publication Data

US 2013/0309319 A1    Nov. 21, 2013

Related U.S. Application Data

(63) Continuation of application No. 12/068,006, filed on Jan. 31, 2008, now Pat. No. 8,945,505.

(60) Provisional application No. 60/899,007, filed on Feb. 2, 2007.

(51) Int. Cl.
*A61K 33/36* (2006.01)
*A61K 45/06* (2006.01)

(52) U.S. Cl.
CPC ............. *A61K 33/36* (2013.01); *A61K 45/06* (2013.01)

(58) Field of Classification Search
CPC ................................ A61K 33/36; A61K 45/06
See application file for complete search history.

(56) References Cited

U.S. PATENT DOCUMENTS

| | | | | |
|---|---|---|---|---|
| 1,498,639 A | * | 6/1924 | Pratt | A01N 59/22 424/620 |
| 3,622,664 A | * | 11/1971 | Brown | A23K 20/30 424/624 |
| 4,677,974 A | * | 7/1987 | Leonardi | A61F 13/124 602/42 |
| 5,362,735 A | | 11/1994 | Luengo | |
| 2004/0022869 A1 | | 2/2004 | Chen et al. | |
| 2005/0163863 A1 | | 7/2005 | Chelbi Alix et al. | |
| 2006/0292243 A1 | | 12/2006 | Hsin | |

FOREIGN PATENT DOCUMENTS

| | | |
|---|---|---|
| CN | 1059909 A | 4/1992 |
| EP | 0911031 A2 | 4/1999 |
| EP | 0804928 B1 | 10/2004 |
| EP | 1 721 615 A1 | 11/2006 |
| EP | 1736161 A2 | 12/2006 |
| JP | 2001-519366 A | 10/2001 |
| JP | 2005206591 A | 8/2005 |
| JP | 2006-206461 A | 8/2006 |
| KR | 2002083458 A | 11/2002 |
| KR | 2002083678 A | 11/2002 |
| WO | 95/01789 A1 | 1/1995 |
| WO | 99/18798 A1 | 4/1999 |
| WO | WO-99/18798 A1 | 4/1999 |
| WO | 03/047524 A2 | 6/2003 |
| WO | WO 2003/066577 A1 | 8/2003 |
| WO | WO 2003/086424 A1 | 10/2003 |
| WO | WO-03/090766 A1 | 11/2003 |
| WO | WO 2006/069293 A2 | 6/2006 |
| WO | 2006/104292 A1 | 10/2006 |
| WO | 2006/121280 A1 | 11/2006 |
| WO | WO-2006/121280 A1 | 11/2006 |

OTHER PUBLICATIONS

He et al. Arsenic Induces NAD(P)H-quinone Oxidoreductase I by Disrupting the Nrf2_Keap1_Cul3 Complex and Recruiting Nrf2_Maf to the Antioxidant Response Element Enhancer, Aug. 18, 2006, Journal of Biological Chemistry, vol. 281 No. 33, pp. 23620-23631.*
A. Tamura, "Studies on Anti-Inflammatory Effect of Arsenic—especially on anti-edematous effect," Shikawa Gakuho, vol. 81, No. 3, Mar. 1981, pp. 511-531.
Canadian Office Action issued in Canadian Application No. 2,677,388 dated Aug. 26, 2013, 3 pages.
Australian Patent Examination Report No. 1 issued in Patent Application No. 2008214084 mailed Jun. 20, 2012.
Australian Patent Examination Report No. 2 issued in Patent Application No. 2008214084 mailed Feb. 11, 2013.
Canadian Office Action issued in Canadian Application No. 2,677,388 dated Jul. 9, 2012, 3 pages.
European Search Report issued in European Patent Application No. 08 714162.8-2123 mailed Jan. 18, 2013.
English Translation of Japanese Notice of Grounds for Rejection issued in Japanese Patent Application No. 2009-548463 dated Jun. 11, 2013.
Shichinohe et al., "Protection Effect by Heat Shock Protein against Small-Intestinal Tissue Injury in Septic Peritonitis of Rats", Journal of the Japanese Society of Intensive Care Medicine, 2001, vol. 8, p. 325-332.
English Translation of Israel Office Action issued in Israeli Patent Application No. 217891 dated Jul. 29, 2012.
Non-Final Office Action issued in U.S. Appl. No. 12/068,006 mailed Mar. 31, 2011.
Final Office Action issued in U.S. Appl. No. 12/068,006 mailed Nov. 14, 2011.

(Continued)

*Primary Examiner* — Ali Soroush (74) *Attorney, Agent, or Firm* — McDermott Will & Emery LLP (57) ABSTRACT

The present invention relates to the use of arsenic compounds such as sodium meta arsenite ($NaAsO_2$), arsenic trioxide ($As_2O_3$), and arsenic hexoxide ($As_4O_6$) or combinations thereof, for the treatment of painful, hyperalgesic and/or inflammatory conditions. The present invention also relates to compositions containing the above arsenic compounds for use in the treatment of pain, inflammation and immunological and autoimmune diseases and disorders.

10 Claims, 1 Drawing Sheet

(56) References Cited

OTHER PUBLICATIONS

Non-Final Office Action issued in U.S. Appl. No. 12/068,006 mailed Oct. 25, 2012.
Norwegian Office Action issued in Norwegian Patent Application No. 20044573 dated Mar. 3, 2014, with English Translation.
Communication pursuant to Article 94(3) EPC European Patent Application No. 10 816 100.1 dated Apr. 7, 2014.
Japanese Office Action issued in Japanese Application No. 2013-097681 dated Jun. 17, 2014.
Korean Office Action issued in Korean Application No. 10-2009-7018389 dated Jun. 26, 2014, w/English translation.
McCabe et al., "Sensitivity of Myelomonocytic Leukemia Cells to Arsenite-Induced Cell Cycle Disruption, Apoptosis, and Enhanced Differentiation is Dependent on the Inter-Relationship between Arsenic Concentration, Duration of Treatment, and Cell Cycle Phase," Journal of Pharmacology and Experimental Therapeutics, American Society for Pharmacology and Experimental therapeutics, U.S., vol. 295, No. 2, Nov. 1, 2000.
Muscarella et al., Differential Activation of the c-Jun N-Terminal Kinase Pathway in Arsenite-Induced Apoptosis and Sensitization of Chemically Resistant Compared to Susceptible B-Lymphoma Cell Lines,: Toxicological Sciences, Acadmeic Press, SanDiego, FL, U.S. vol. 68, No. 1, Jul. 1, 2002, pp. 85-92.
Hershko et al., "Arsenite inhibits interleukin-6 production in human intestinal epithelial cells by down-regulating nuclear factor kB activity," Clinical Science, Oct. 2002, vol. 103, No. 4, Oct. 2002, pp. 381-390.
Sakurai et al., "Evaluation of immunotoxic and immunodisruptive effects of inorganic arsenite on human monocytes/macrophages," Internatonal Immunopharmacology Elsevier, Amsterdam NL, vol. 4, No. 13, Jan. 1, 2004, pp. 1661-1673.
L. Institoris et al., "Detection of the effects of repeated dose combined propoxur and heavy metal exposure by measurement of certain toxicological, haematological and immune function parameters in rats," Toxicology, vol. 163, pp. 185-193, 2001 Elsevier.
European Search Report issued in European Application No. 14166070.4 dated Jul. 9, 2014.
Chinese Office action issued in Chinese Application No. 201310522816.6 dated Oct. 28, 2014, w/English translation.
Japanese Office Action issued in Japanese Application No. 2013-097681 mailed Dec. 9, 2014, with English Translation.
Chinese Decision of Reexamination issued in Chinese Application No. 200880003873.0 dated Jan. 22, 2015, with English Translation.
Yasuo Shichinohe et al., "Abdominal sepsis induces expression of heat shock protein 70s 9HSP70) and heat shock response prevents septic gut mucosal injury of the rats", Journal of the Japanese Society of Intensive Care Medicine, 2001, vol. 8, p. 325-332, with English Abstract.
Dan D. Hershko et al., "Arsenite inhibits interleukin-6 production in human intestinal epithelial cells by down-regulating nuclear factor-kβ activity", The Biochemical Society and the Medical Reseach Society, 2002, pp. 381-390.
Office Action Canadian Patent Application No. 2,845,292 dated May 5, 2015.
Office Action Canadian Patent Application No. 2,677,388 dated Apr. 23, 2015.
Notification of the Second Office Action Chinese Patent Application No. 201310522816.6 dated Jul. 7, 2015 with English translation.
Canadian Office Action dated Feb. 22, 2016 issued in Canadian Patent Application No. 2,677,388.
Canadian Office Action dated Apr. 27, 2016 issued in Canadian Patent Application No. 2,845,292.
Chinese (Third) Office Action issued in Chinese Patent Application No. 200880003873.0, dated Dec. 15, 2015, with English translation.
Written Opinion & Search Report issued by Intellectual Property Office of Singapore in Singaporean Patent Application No. 10201405278S, dated Nov. 17, 2015.

Samuel Waxman, et al., "History of the Development of Arsenic Derivatives in Cancer Therapy", The Oncologist, 2001, vol. 6, Suppl. 2, pp. 3-10.
Mexican Office Action issued in Mexican Patent Application No. Mx/a/2009/008174 dated Aug. 21, 2013.
Chinese Office Action, and English translation thereof, issued in Chinese Patent Application No. 200880003873.0 dated Jan. 29, 2012.
Vahidnia, A. et al. "Arsenic-induced toxicity: effect on protein composition in sciatic nerve". Human & Experimental Toxicology. Jul. 25, 2006. vol. 25. pp. 667-674.
Garcia-Chavez, E. et al. "Lipid Oxidative Damage and Distribution of Inorganic Arsenic and its Metabolites in the Rat Nervous System After Arsenite Exposure: Influence of Alpha Tocopherol Supplementation". NeuroToxicology. May 1, 2006. pp. 1024-1031.
European Office Action issued in Corresponding European Patent Application No. 08 714 162.8 dated Mar. 1, 2012.
English translation of Russian Office Action issued in Russian Patent Application No. 2009132951/15 dated Feb. 17, 2012.
Vuky, J. et al. "Phase II trial of Arsenic Trioxide in Patients with Metastatic Renal Cell Carcinoma". Investigational New Drugs. Aug. 2002. vol. 20. pp. 327-330.
Beer, T. et al. "Southwest Oncology Group Phase II Study of Arsenic Trioxide in Patients with Refractory Germ Cell Malignancies". American Cancer Society. May 10, 2006. pp. 2624-2629.
Hussein, M. "Phase II Study of Arsenic Trioxide in Patients with Relapsed or Refractory Multiple Myeloma". British Journal of Haematology. Feb. 9, 2004. vol. 125. pp. 470-476.
Schiller, G. et al. "Phase II Multicenter Study of Arsenic Trioxide in Patients with Myelodysplastic Syndromes". Journal of Clinical Oncology. Dec. 16, 2005. vol. 24. pp. 2456-2464.
Munshi, NC. et al. "Cliunical Activity of Arsenic Trioxide for the Treatment of Multiple Myeloma". Leukemia. 2002. vol. 16. pp. 1835-1837.
Litzow, M. et al. "A Phase II Trial of Arsenic trioxide for Relapsed and Refractory Acute Lymphoblastic Leukemia". Haematologica/The Haematologicy Journal. Aug. 2006. vol. 91. No. 8. pp. 1105-1108.
Kim, K. et al. "A Phase II Trial of Arsenic Trioxide in Patients with Metastatic Melanoma". Cancer. May 23, 2005. pp. 1687-1692.
"Quantitative Analysis of Hepatic Enzyme Histochemistry in Rat with Subacute Liver Injury Induced by Yellpw Phosphorus and Sodium Arsenite: (I) the Changes of Marker Enzymes in Mitochondria". Jun. 30, 1999.
"One Case of Sodium Arsenite Poisoning-induced Torsades de Pointes Ventricular Tachycardia". Dec. 31, 1997.
Israel Office Action issued in Israeli Patent Application No. 200173 dated Jul. 29, 2012.
English translation of Japanese Notice of Grounds for Rejection issued in Japanese Patent Application No. 2009-548463 dated Jan. 8, 2013.
Chinese Office Action, and English translation thereof, issued in Taiwanese Patent Application No. 097104110 dated Nov. 8, 2012.
Ishii, Y. Shika-Gwakuho, 1986, V86 N5, P713-731.
Ishii, Y., Japanese Journal of Pharmacology, 1984, V36 N. Suppl., P216P.
Hershko, Dan. "Arsenite inhibits interleukin-6 production in human intestinal epithelial cells by down-regulating nuclear factor-kB activity." The Biochemical Society and the Medical Research Society. 2002. V. 103. pp. 381-390.
De Jongh, R. et al. "The Role of Interleukin-6 in Nociception and Pain." Then International Anesthesia Research Society. 2003. pp. 1096-1103.
Holleman-Wiberg. "Inorganic Chemistry." Academic Press. 2001. p. 749.
Finn, P. et al. "Molecular Profiling of the Role of the NF-kB Family of Transcription Factors During Alloimmunity." Journal of Leukoeyte Biology. V. 72. Nov. 2002. pp. 1054-1062.
Villar, J. "Heat Shock Protein Gene Expression and Survival in Critical Illness." CCForum. Jan. 24, 2000. http://ccforum.com/content/4/1/002.
New Zealand Office Action issued in New Zealand Patent Application No. 578621, mailed Mar. 23, 2011.

(56) References Cited

OTHER PUBLICATIONS

International Preliminary Report on Patentability issued in International Patent Application No. PCT/US2008/052751, mailed Nov. 3, 2009.
European Search Report issued in European Patent Application No. 08 714 162.8-2123, mailed Mar. 4, 2011.
PCT/ISA/206, issued in International Application No. PCT/US2008/052751, mailed Jul. 16, 2008.
Ishii, Y., "Studies on Relationships between As2O3-induced Analgesia and Monoamine Levels in the Brain of a Mouse," 1986, p. 713-731, vol. 86, No. 5, XP009099577.
Ishii, Y., et al., "Relationships between As2O3-induced analgesia and monoamine in mouse brain," Japanese Journal of Pharmacology, 1984, p. 216P, vol. 36, No. Suppl. XP009099578.
García-Chávez, E., et al., "Lipid oxidative damage and distribution of inorganic arsenic and its metabolites in the rat nervous system after arsenite exposure: Influence of alpha tocopherol supplementation," NeuroToxicology, Dec. 5, 2006, p. 1024-1031, vol. 27, No. 6, XP005792766, Elsevier Inc.
Vahidnia, A., et al., "Arsenic-induced toxicity: effect on protein composition in sciatic nerve," Human & Experimental Toxicology, Nov. 2006, p. 667-674, vol. 25 No. 11, XP-002479000, SAGE Publications.
Mavromatis, B. H., et al., "The Impact of GM-CSF on Arsenic Trioxide (As2O3, Trisenox) Therapy in Patients with Myelodysplastic Syndrome (MDS): Preliminary Results of a Phase II Study," Blood, Nov. 16, 2006, p. 299B, vol. 108, No. 11(2), XP009099580, American Society of Hematology.
Kim, K. B., et al., "A Phase II Trial of Arsenic Trioxide in Patients with Metastatic Melanoma," Cancer, Oct. 15, 2005, p. 1687-1692, vol. 104, No. 8, XP-002479001, American Cancer Society.
Au, Wing Y., "In vitro and in vivo activity of arsenic trioxide in non-Hodgkin lymphoma," Proceedings of the American Association for Cancer Research Annual Meeting, Apr. 2006, p. 1238, vol. 47, XP001538423.
International Search Report and Written Opinion of the International Searching Authority issued in International Patent Application No. PCT/US2008/052741 dated Feb. 5, 2009.
Yin et al "Experimental Study on the Therapeutic Mechanism of Arsenic Trioxide(AS2O3) for Bronchial Asthma" pp. 662-665 vol. 28 No. 30, Published 2002.
Yao et al "Molecular Mechanism of Arsenic Trioxide in Preventing and Treating Airway Inflammation of Asthma: Effects of Arsenic trioxide on the Gene Expression of Mitogen-Activated Protein Kinease Phosphatese" p. 6652-6653 Chinese Journal of Clinical Rehabilitation vol. 8 No. 30, Oct. 25, 2004.
Zhou et al "Effect of Arsenic Trioxide on Apoptosis of Pulmonary Eosinophile in Asthamatic Guinea-pigs" p. 292-294 Medline vol. 22.
Akira Tanura "Studies on Anti-inflamatory Efect of Arsenic—Especially on Anti-Edematous Effect" pp. 511-531 Journal of Tokyo Dental College Society, vol. 81, No. 3 Mar. 1, 1981.
Li et al "TheraPeutic Effect of Sodium Arsenite on Rheumatoid Arthritis in Rats" pp. 348-351 Chinese Journal of Pathophysioloy vol. 23 No. 2 Jan. 1, 2007.
Notification of Transmittal of International Preliminary Report on Patentability and Written Opinion issued in International Application No. PCT/US2008/052751 dated Nov. 3, 2009.
Chinese Office Action, w/ English translation thereof, issued in Chinese Patent Application No. CN 200880003873.0 dated Apr. 19, 2011.
Hunan Medical Journal, vol. 16, No. 3, Jun. 1999, pp. 175-176.
J Clin Cardiol (China), Dec. 31, 1997, vol. 13, No. 1, pp. 8.
Munshi, Nc. et al. "Clinical Activity of Arsenic Trioxide for the Treatment of Multiple Myeloma". Leukemia. 2002. vol. 16. pp. 1835-1837.
"Quantitative Analysis of Hepatic Enzyme Histochemistry in Rat with Subacute Liver Injury Induced by Yellow Phosphorus and Sodium Arsenite: (I) the Changes of Marker Enzymes in Mitochondria". Jun. 30, 1999.
Matthews, V. et al. " Single-agent Arsenic Trioxide in the Treatment of Newly Diagnosed Acute Promyelocytic Leukemia: Durable Remissions with Minimal Toxicity". Blood. Apr. 1, 2006. vol. 107. No. 7. pp. 2627-2631.
Vey, N. et al. "Arsenic Trioxide in Patients with Myelodys plastic Syndromes: A Phase II Multicenter Study". Journal of Clinical Oncology. Jun. 1, 2006. vol. 24. pp. 2465-2471.
Ribeiro et al., "Sodium Arsenite Induces Heat Shock Protein-72 Kilodalton Expression in the Lungs and Protects Rats Against Sepsis", Jun. 1994, Crit Care Med, vol. 22, Iss. 6, pp. 922-929.
Harrison et al., "Immunosuppression by Arsenic: a Comparison of Cathepsin L Inhibition and Apoptosis", 2001, International Immunopharmacology, vol. 1, pp. 647-656.
"Dictionary", Published 1980, The Random House College, p. 683.
United States Office Action issued in U.S. Appl. No. 12/068,006 dated Jul. 30, 2013.
Hossain et al., "Arsenite Induces Apoptosis of Murine T Lymphocytes Through Membrane Raft-Linked Signaling for Activation of c-Jun Amino-Terminal Kinase", J. Immunol., vol. 165, No. 8, pp. 4290-4297 (2000).

\* cited by examiner

USE OF ARSENIC COMPOUNDS FOR TREATMENT OF PAIN AND INFLAMMATION

This application is a Continuation application of U.S. Ser. No. 12/068,006, filed Jan. 31, 2008, now U.S. Pat. No. 8,945,505, which claims priority to provisional application Ser. No. 60/899,007, filed Feb. 2, 2007, the disclosures of which applications are incorporated herein in their entirety.

FIELD OF THE INVENTION

This invention relates to methods and compositions for treating pain and inflammation, as well as treating autoimmune and immunological disorders using arsenic compounds. More particularly, the methods and compositions of the present invention relate to the use of sodium meta arsenite ($NaAsO_2$), arsenic trioxide ($As_2O_3$), and/or arsenic hexoxide ($As_4O_6$) or salts thereof, to treat pain, inflammation, and autoimmune and immunological disorders.

BACKGROUND OF THE INVENTION

Pain perception, or nociception, is mediated by the peripheral terminals of a group of specialized sensory neurons, termed nociceptors. A wide variety of physical and chemical stimuli induce activation of such neurons in mammals, leading to recognition of a potentially harmful stimulus. Inappropriate or excessive activation of nociceptors, however, can result in debilitating acute or chronic pain.

Generally pain is experienced when the free nerve endings which constitute the pain receptors in the skin as well as in certain internal tissues are subjected to mechanical, thermal, chemical or other noxious stimuli. The pain receptors can transmit signals along afferent neurons into the central nervous system and thence to the brain.

The causes of pain can include inflammation, physical injury, infectious disease, chemical or anoxic injury, muscle spasm and the onset of a neuropathic event or syndrome. Ineffectively treated pain can be devastating to the person experiencing it by limiting function, reducing mobility, complicating sleep, and dramatically interfering with the quality of life.

Inflammation is a physiological condition characterized in the acute form by the classical signs of pain, heat, redness, swelling and loss of function. Inflammatory pain can occur when tissue is damaged. For example, physical, chemical, and thermal events, surgery, infection and autoimmune diseases can cause tissue damage and inflammation. When a tissue is damaged, a host of endogenous pain-inducing substances, for example bradykinin and histamine can be released from the injured tissue. The pain-inducing substances can bind to receptors on the sensory nerve terminals and thereby initiate afferent pain signals.

Additionally, pain-inducing substances can be released from nociceptive afferent terminals, and neuropeptides released from sensory terminals can accentuate an inflammatory response. Thus, during inflammation there can be a sprouting of peptidergic peripheral fibers and an increased content of peptide, with many fibers showing a coexistence of substance P (SP) and calcitonin gene related peptide (CGRP). Substance P can induce contraction of endothelia cells, which in turn causes plasma extravasation to allow other substances (bradykinin, AIP, histamine) to gain access to the cite of injury and the afferent nerve terminals. Substance P release by the sensory nerve terminal can also degranulate mast cells. This process is thought to be an important factor in neurogenic inflammation due to the release of inflammatory mediators such as histamine and serotonin and the release of proteolytic enzymes which catalyze the production of bradykinin. CGRP apparently does not produce plasma extravasation, but is a powerful vasodilator and also acts synergistically with SP and other inflammatory mediators to enhance plasma extravasation. All the above listed inflammatory mediators can either sensitize nociceptors or produce pain. Hence, inhibition of the inflammatory mediators' release and/or activity can be useful in the treatment of common inflammatory diseases such as, for example, asthma, arthritis, dermatitis, rhinitis, cystitis, gingivitis, thrombo-phlelitis, glaucoma, astro-intestital diseases or migraine.

Although inflammatory pain is generally reversible and subsides when the injured tissue has been repaired or the pain inducing stimulus removed, present methods for treating chronic inflammatory pain have many drawbacks and deficiencies. Thus, the typical oral, parenteral or topical administration of an analgesic drug to treat the symptoms of pain, for example, an antibiotic to treat inflammatory pain causing factors, can result in widespread systemic distribution of the drug and undesirable side effects. Additionally, current therapy for inflammatory pain suffers from short duration of drug efficacy, which necessitates frequent drug re-administration with possible resulting increasing drug tolerance and resistance, antibody development and/or drug dependence and addiction, all of which are unsatisfactory. Furthermore, frequent drug administration increases the expense of the regimen to the patient and can require the patient to remember to adhere to a dosing schedule.

Examples of treatments for inflammation and muscle pain include non-steroidal anti-inflammatory drugs (NSAIDs), including aspirin and ibuprofen; and opioids, such as morphine.

NSAIDs alleviate pain by inhibiting the production of prostaglandins released by damaged tissues. Prostaglandins have been shown to be peripheral mediators of pain and inflammation, as in arthritic diseases, and a reduction in their concentration provides relief to patients. It has been suggested that prostaglandins are involved in the mediation of pain in the spinal cord and the brain, which may explain the analgesic effects of NSAIDS in some pain states that do not involve inflammation or peripheral tissue damage. However, prostaglandins are only one of several mediators of pain. As such, NSAIDs have a ceiling of activity above which increasing doses do not give more pain relief.

Furthermore, NSAIDs have side effects that limit their usefulness. For example, they can cause irritation of the gastro-intestinal tract and prolonged use may lead to the development of extensive ulceration of the gut. This is particularly true in elderly patients who frequently use NSAIDs for their arthritis conditions.

The therapeutic actions of opioids are on the central nervous system including the brain and spinal cord. Opioids inhibit the efficiency of neurotransmission between the primary sensory afferents (principally C-fibers) and the projection neurons. They achieve this by causing a prolonged hyperpolarization of both elements of these synapses. The use of opioids is effective in alleviating most types of acute pain and chronic pain caused by the malignant tumors. There are, however, a number of chronic malignant pain conditions that are partly or completely refractory to opioid analgesia, particularly those that involve nerve compression, e.g. by tumor formation and growth. Unfortunately opioids also have unwanted side-effects including depression of the respiratory system, constipation, and psychoactive effects including sedation, euphoria and drug dependency. These side effects occur at doses similar to those that produce analgesia and, therefore, limit the doses that can be given to patients. Additionally, opioids such as morphine and heroin are well-known drugs of abuse that often lead to rapid increase in drug tolerance and physical dependence. With the development of tolerance, the dose and frequency of drug required to produce the same analgesic effect increases with time. This may lead to a condition in which the doses required to alleviate the chronic unremitting pain can be life-threatening due to previously mentioned side-effects. As used herein, the term "chronic" means pain lasting for one month duration or longer. "Acute pain" is defined as pain of shorter duration than chronic pain and of high intensity.

Although pain arising from inflammation and muscle spasm can be initiated by mechanical or chemical stimulation of the primary sensory neuron free terminal, neuropathic pain does not require an initial stimulus to the peripheral, free nerve terminal. Neuropathic pain is a persistent or chronic pain syndrome that can result from damage to the nervous system, the peripheral nerves, the dorsal root ganglion, dorsal root, or to the central nervous system.

Neuropathic pain involves pain signal transmission in the absence of stimulus, and typically results from damage to the nervous system. In most instances, such pain is thought to occur because of sensitization in the peripheral and central nervous systems following initial damage to the peripheral system (e.g., via direct injury or systemic disease). Neuropathic pain is typically burning, shooting, and unrelenting in its intensity and can sometimes be more debilitating that the initial injury or disease process that induced it.

Existing treatments for neuropathic pain are largely ineffective. Opiates, such as morphine, are potent analgesics, but their usefulness is limited because of adverse side effects mentioned earlier, such as rapid development of drug tolerance, physical addictiveness and withdrawal properties, as well as respiratory depression, mental status changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to significant side effects.

Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is often characterized by spontaneous burning pain combined with hyperalgesia and allodynia.

Unfortunately, there is no existing method for adequately, predictably and specifically treating established neuropathic pain (Woolf C. et al., Neuropathic Pain: A etiology, Symptoms, Mechanisms, and Management, Lancet 1999; 353: 1959-64) as present treatment methods for neuropathic pain consists of merely trying to help the patient cope through psychological or occupational therapy; rather than by reducing or eliminating the pain experienced.

Therefore, there remains a need for an improved method or compound for the treatment of unremitting chronic and acute pain, including inflammatory pain. There is also a need for improved methods and agents for treatment of immunological and autoimmune diseases and conditions. This is achieved by administration of arsenic compounds, in accordance with this disclosure.

SUMMARY OF THE INVENTION

The present invention addresses the limitations noted for the background art and provides new methods for reducing inflammation and/or chronic, acute, and/or and/or pain. The present invention is based, in part, on the discovery and demonstration that arsenic compounds such as sodium meta arsenite ($NaAsO_2$), arsenic trioxide ($As_2O_3$), and/or arsenic hexoxide ($As_4O_6$) or salts thereof, may be used to reduce inflammation and pain.

This disclosure, according to an aspect of the invention, provides methods for treating a mammal (e.g., a human) suffering from chronic, and/or acute. In accordance with certain embodiments of this aspect of the invention, the disclosure provides methods for the use of arsenic compounds, preferably sodium meta arsenite ($NaAsO_2$), arsenic trioxide ($As_2O_3$)/and/or arsenic hexoxide ($As_4O_6$) or salts thereof, to treat or prevent pain including, for example, visceral pain (such as pancreatitis), cancer related pain (such as metastatic cancer), central pain syndromes (such as the pain caused by stroke), postsurgical pain syndromes (e.g, postmastectomy syndrome), bone and joint pain (osteoarthritis), spine pain (e.g., acute and chronic low back pain), myofascial pain (muscular injury), postoperative, perioperative pain and preemptive analgesia, chronic pain, dysmenorrhea, as well as pain associated with angina, and inflammatory pain of varied origins (e.g., asthma, osteoarthritis, rheumatoid arthritis).

In an exemplary embodiment, the invention provides the use of sodium meta arsenite ($NaAsO_2$), arsenic trioxide ($As_2O_3$), and/or arsenic hexoxide ($As_4O_6$) or salts thereof, in the preparation of topical, oral or parenteral composition to treat acute and chronic hyperalgesia.

Within an aspect of the invention is provided a method for treating inflammation, comprising administering a therapeutically sufficient amount of an inorganic arsenic compound, e.g., sodium meta-arsenite (NaAsO2), arsenic trioxide ($As_2O_3$); and/or arsenic hexoxide (As4O6) to a mammal, wherein administration of the compound results in a clinically significant improvement in the inflammatory condition of the mammal. Within an embodiment of the invention, the clinically significant improvement in the inflammatory condition includes one or more of the following:

a) a decrease or inhibition in pain; b) a decrease or inhibition in swelling; c) a decrease or inhibition in redness; d) a decrease or inhibition in temperature of an affected tissue; and e) and a decrease or inhibition in loss of function.

It is theorized, but not relied on for the purpose of this invention, that histamine, cytokinins and other polypeptides release is likely to occur in inflammatory conditions, such as in lungs of asthma patients. Accordingly, in an embodiment, the methods of the invention involve local or systemic administration of sodium meta-arsenite to treat inflammation and/or tissue damage displayed in, for example, asthmatic airways and cancer related necrosis.

In another embodiment, the methods of the invention provide local administration of sodium meta-arsenite, arsenic trioxide and/or arsenic hexoxide to treat inflammation at a damaged-tissue site on an individual.

In other embodiments, the invention provides methods of treating pain and/or tissue damage associated with inflammation, e.g., tissue fibrosis in cancer related or autoimmune induced disease. Examples of immune and autoimmune diseases that may be treated by the present methods include immune and autoimmune disease of the endocrine, neuro-muscular, connective tissue, cardio-pulmonary, skeletal and gastrointestinal systems. In particular, the arsenic compounds of the invention may be used to treat autoimmune disorders and immunologically mediated disorders such as multiple sclerosis and other immune related conditions.

In another embodiment, inflammation and pain caused by infectious disease, including bacterial, viral, parasitic infections are treated by the methods of the invention.

The methods of the invention comprise administering a therapeutically effective amount of sodium meta arsenite, arsenic trioxide and/or arsenic hexoxide, as appropriate. In preferred embodiments, the therapeutic amount is in the range of from about 10 µg to about 200 mg, preferably in divided doses which are administered parenterally, intrathecally, orally, via inhalation or topically. A preferred-total daily-dose is from about 0.5 mg to about 70 mg; most preferably about 10 mg/kg.

It is further theorized, but not relied on for the purpose of this invention, that sodium meta-arsenite, arsenic trioxide and/or arsenic hexoxide inhibits and/or depletes leucocytes and lymphocytes that are involved in producing autoimmune antibodies and damaging tissues. Accordingly, in an exemplary embodiment, the methods of the invention provide local or systemic administration of sodium meta-arsenite, arsenic trioxide and/or arsenic hexoxide to treat autoimmune induced inflammations and/or tissue damage.

The term "hyperalgesia" or "hyperalgesic sensation" as used herein refers to an extreme sensitivity to pain, which in one form is caused by damage to nociceptors in the body's soft tissues. Hyperalgesia can be experienced in focal, discrete areas, or as a more diffuse, body-wide form. Conditioning studies have established that it is possible to experience a learned hyperalgesia of the latter, diffuse form. The focal form is typically associated with injury, and is divided into two subtypes: Primary hyperalgesia describes pain sensitivity that occurs directly in the damaged tissues. Secondary hyperalgesia describes pain sensitivity that occurs in surrounding undamaged tissues.

It is to be understood that both the foregoing general description and the following detailed description are exemplary and explanatory only and are not restrictive of the invention, as claimed.

DETAILED DESCRIPTION OF THE INVENTION

This invention provides methods of treating a mammal (e.g., a human) suffering from pain and/or inflammatory diseases or conditions. In particular embodiments, such methods include local or systemic administration of arsenic compounds, preferably sodium meta arsenite ($NaAsO_2$), arsenic trioxide ($As_2O_3$), and/or arsenic hexoxide ($As_4O_6$) or salts thereof, to treat inflammation and acute and/or chronic pain.

In certain embodiments, sodium meta arsenite ($NaAsO_2$), arsenic trioxide ($As_2O_3$), and/or arsenic hexoxide ($As_4O_6$) or salts thereof are used to treat or prevent pain including, for example, visceral pain (such as pancreatitis, interstitial cystitis, renal colic, prostatitis, chronic pelvic pain) cancer related pain, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and post-surgical pain syndromes (e.g., post-mastectomy syndrome, post-thoracotomy syndrome, stump pain), bone and joint pain (osteoarthritis), spinal pain (e.g., acute and chronic low back pain, neck pain, spinal stenosis), shoulder pain, repetitive motion pain, acute pain such as dental pain, sore throat, cancer pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins including immunological reactions and autoimmune diseases (e.g., osteoarthritis, rheumatoid arthritis, rheumatic disease, teno-synovitis and gout, ankylosing spondylitis, bursitis, Lupus).

Arsenic compounds of the present invention may also be used for the treatment of headache including cluster headache, migraine including prophylactic and acute use, stroke, closed head trauma, cancer, sepsis, gingivitis, osteoporosis, benign prostatic hyperplasia and hyperactive bladder.

The skilled artisan will appreciate that pain is a heterogeneous disorder. In the methods and compositions according to the invention, the term "pain" shall refer to all types of pain, including acute and persistent pain. Preferably, the term shall refer to persistent pains, such as, but not limited to, diabetic neuropathy, fibromyalgia, pain associated with somatoform disorders, arthritic pain, cancer pain, neck pain, shoulder pain, back pain, cluster headaches, tension-type headache, migraine; herpes neuralgia, phantom limb pain, central pain, dental pain, NSAID-resistant pain, visceral pain, surgical pain, post-operative pain, bone injury pain, pain during labor and delivery, pain resulting from burns, including sunburn, post-partum pain, angina pain, and genitourinary tract-related pain including cystitis. The term persistent pain shall also preferably refer to nociceptive pain or nociception.

Within another aspect of the invention is provided a method for treating inflammation, comprising administering a therapeutically sufficient amount of an inorganic arsenic compound, e.g., sodium meta-arsenite ($NaAsO2$) to a mammal, wherein administration of the compound results in a clinically significant improvement in the inflammatory condition of the mammal. Within an embodiment of the invention, the clinically significant improvement in the inflammatory condition includes one or more of the following: a) a decrease or inhibition in pain; b) a decrease or inhibition in swelling; c) a decrease or inhibition in redness; d) a decrease or inhibition in heat; and e) and a decrease or inhibition in loss of function.

Asthma is a disease of the airways that contains elements of both inflammation and broncho constriction. Treatment regimens for asthma are based on the severity of the condition. Mild cases are either untreated or are only treated with inhaled beta (B)-agonists which affect the bronchoconstriction element, whereas patients with more severe asthma typically are treated regularly with inhaled corticosteroids which to a large extent are anti inflammatory in their nature.

In certain other embodiments of the invention, sodium meta-arsenite is used to treat or prevent hyperreactive airways and to treat or prevent inflammatory events associated with airways disease, e.g., asthma including allergic asthma (atopic or non-atopic), as well as exercise-induced bronchoconstriction, occupational asthma, viral-or bacterial exacerbation of asthma, other non-allergic asthmas and "wheezy-infant syndrome."

Chronic obstructive pulmonary disease (COPD) is another common disease with inflammatory and bronchoconstrictive components. The disease is potentially lethal, and the morbidity and mortality from the condition is considerable. At present, there is no known pharmacological treatment capable of changing the course of the disease.

The arsenic compounds of the invention, e.g., sodium meta arsenite in accordance with an exemplary embodiment of the present invention, may also be used to treat chronic obstructive pulmonary disease including emphysema, adult respiratory distress syndrome, bronchitis, pneumonia, allergic rhinitis (seasonal and perennial), and vasomotor rhinitis. It may also be effective against pneumoconiosis, including aluminosis, anthracosis, asbestosis, chalicosis, ptilosis, siderosis, silicosis, tabacosis, and byssinosis.

Furthermore, the arsenic compounds of the invention, such as sodium meta aresenite, in accordance with other embodiments of the present invention, may be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema. It may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). The arsenic compounds of the invention, preferably, sodium meta aresenite, may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, ea. Parkinson's and Alzheimer's disease, epilepsy, septic shock e.g. as anti-hypovolemic and/or anti-hypotensive agents.

In another embodiment, the arsenic compounds of the invention are used to prevent and/or treat inflammatory liver disease, or multiple sclerosis.

Another embodiment provides, in accordance with the invention, the use of arsenic compounds, in particular sodium meta-arsenite, in a topical composition to treat, reduce, or prevent local inflammation. In an embodiment, the arsenic compound, e.g., sodium meta-arsenite is administered to a mammal to reduce or prevent histamine release.

In other embodiments, in accordance with the present invention, sodium meta-arsenite or other arsenic compound (s) of the invention is administered to a mammal (e.g., a human) to treat or reduce inflammation symptoms associated with immune-mediated and/or autoimmune diseases such as, for example, systemic lupus erythematosus (SLE), autoimmune rheumatoid arthritis (RA), systemic vasculitis; insulin-dependent diabetes mellitus (IDDM; type I diabetes, inflammatory bowel disease (IBD), graft versus-host disease (GVHD), celiac disease, autoimmune thyroid disease, Sjögren's syndrome, autoimmune gastritis, ulcerative colitis; Crohn's disease; autoimmune hepatitis, primary biliary cirrhosis; primary sclerosing cholangitis; cutaneous autoimmune diseases, autoimmune dilated cardiomyopathy, multiple sclerosis (MS), myasthenia gravis (MG), vasculitis (e.g., Takayasu's arteritis and Wegener's granulomatosis), autoimmune diseases of the muscle, autoimmune neuromuscular disorders, such as ankylosing spondylitis, multiple sclerosis, and acute disseminated encephalitis; immune mediated neuropathies; autoimmune diseases of testis, autoimmune ovarian disease, autoimmune uveitis, Graves' disease, psoriasis, ankylosing spondyitis, Addison disease, Hashimoto thyroiditis, idiopathic thrombocytopenic purpura, autoimmune lung disease such as Wegener's disease and Churg-Strauss syndrome; immunologic lung diseases such as asthma, infiltrative lung disease, hypersensitivity lung disease and sarcoidosis; dermatomyosis including scleroderma and polymyosis; and vitiligo.

The methods of the invention are expected to slow or stop the progression of inflammation, improve at least some symptoms, functioning, and/or increase survival and recovery.

According to certain other aspect of the present invention, sodium meta arsenite ($NaAsO_2$), arsenic trioxide ($As_2O_3$), and/or arsenic hexoxide ($As_4O_6$) or salts thereof, may be used to inhibit and or deplete leucocytes or lymphocytes and their secretions, which are associated to the onset of autoimmune disorders in a human. According to one embodiment of this aspect of the invention, administration of sodium meta-arsenite can result in a reduction in the levels of auto antibodies, B cells producing auto antibodies, and/or auto reactive T cells. The reduction in any of these cell types or their secretions can be, for example, at least 10%, 20%, 30%, 50%, 70%, or more as compared to pretreatment levels.

In accordance with the present invention, arsenic compounds of the invention can be used alone or in combination with other known pain and/or anti-inflammatory medications such as, for example, NSAIDs. Combinations of arsenic compounds are also contemplated.

Animal models of the above-mentioned diseases and conditions are generally known in the art, and may be suitable for evaluating compounds of the present invention for their potential utilities. Finally, compounds of the present invention are also useful as research tools (in vivo and in vitro).

The methods of the invention can be used to treat a mammal that has pain and/or inflammation, e.g., rheumatoid arthritis-associated pain or asthma-associated inflammation. Examples of mammals include humans or other primates (e.g., chimpanzees), rodents (e.g., mice, rat, or guinea pigs), rabbits, cat, dogs, horses, cows, and pigs. In some of the subjects afflicted, the treatment is expected to result in inhibiting the progression of, and improvement in pain and/or inflammation symptoms.

Method of Administration

Any suitable mode of administration may be used in accordance with the present invention including, but not limited to parenteral administration such as intravenous, subcutaneous, intramuscular and intrathecal administration; oral, intranasal, rectal or vaginal administration may also be used; directly into the tumor; transdermal patches; implant devices (particularly for slow release); inhalers, long-acting depot administration, and finally, topical administration may be used. The mode of administration will vary according to the type of arsenic compound being used and the disease to be treated.

The pharmaceutical compositions to be used may be in the form of sterile physiologically acceptable (aqueous or organic) solutions, colloidal suspensions, creams, ointments, pastes, capsules, caplets, tablets and cachets. The pharmaceutical compositions comprising arsenic compounds of the invention can be contained in sealed sterile glass containers and/or ampoules. Further, the active ingredient may be micro-encapsulated, encapsulated in a liposome, noisome or lipofoam alone or in conjunction with targeting antibodies. It should be recognized that delayed slow or sustained release forms of administration are also included.

Formulation

The arsenic compounds of the invention may be formulated into pharmaceutical preparations for administration to mammals for treatment of pain and inflammation.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Such formulations are sterile. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers of therapeutically effective amounts of the arsenic compounds in pharmaceutically acceptable form. The arsenic compound in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes. The kit may also include another therapeutic agent(s) for the treatment of pain and/or inflammation in an appropriate amount. Such other therapeutic agent may be formulated as a combination drug with the arsenic compound contained in the kit, or may be formulated separately.

In another embodiment, a kit of the invention further comprises a needle or syringe, preferably packaged in sterile form, for injecting the complex, and/or a packaged alcohol pad. Instructions are optionally included for administration of arsenic compounds by a clinician or by the patient.

The magnitude of a therapeutic dose of an arsenic compound in the acute or chronic management of pain and/or inflammation will vary with the severity of the condition to be treated and the route of administration. The dose, and perhaps dose frequency, will also vary according to the age, body weight, condition and response of the individual patient. In general, the total daily dose ranges for the conditions described herein are generally from about 10 µg to about 200 mg administered in divided doses administered parenterally or orally or topically. A preferred total daily dose is from about 0.5 mg/kg to about 70 mg/kg of the active ingredient; and most preferably about 10 mg/kg.

Effective dosage achieved in one animal may be converted for use in another animal, including humans, using conversion factors known in the art. See, e.g., Freireich et al., Cancer Chemother. Reports 50(4):219-244 (1966) and Table 1 for equivalent surface area dosage factors.

TABLE 1

| To: | From: | | | | |
|---|---|---|---|---|---|
| | Mouse (20 g) | Rat (150 g) | Monkey (3.5 kg) | Dog (8 kg) | Human (60 kg) |
| Mouse (20 g) | 1 | 0.5 | 0.25 | 0.17 | 0.08 |
| Rat (150 g) | 2 | 1 | 0.5 | 0.25 | 0.14 |
| Monkey (3.5 kg) | 4 | 2 | 1 | 0.6 | 0.33 |
| Dog (8 kg) | 6 | 4 | 1.7 | 1 | 0.5 |
| Human (60 kg) | 12 | 7 | 3 | 2 | 1 |

Desirable blood levels may be maintained by a continuous infusion of an arsenic compound as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

Again, any suitable route of administration may be employed for providing the patient with an effective dosage of an arsenic compound. For example, oral, rectal, vaginal, transdermal, parenteral (subcutaneous, intramuscular, intrathecal and the like) may be employed. Dosage forms include tablets, troches, cachet, dispersions, suspensions, solutions, capsules, patches, and the like. (See, Remington's Pharmaceutical Sciences.)

The pharmaceutical compositions of the present invention comprise an arsenic compound as the active ingredient, or a pharmaceutically acceptable salt thereof, and may also contain a pharmaceutically acceptable carrier, and optionally, other therapeutic ingredients, for example conventional medications for pain therapy. The term "pharmaceutically acceptable salts" refers to salts prepared from pharmaceutically acceptable non-toxic acids and bases, including inorganic and organic acids and bases.

The pharmaceutical compositions include compositions suitable for oral, rectal, mucosal routes, transdermal, parenteral (including subcutaneous, intramuscular, intrathecal and intravenous), although the most suitable route in any given case will depend on the nature and severity of the condition being treated.

In the case where an intravenous injection or infusion composition is employed, a suitable dosage range for use is, e.g., from about 0.5 mg to about 150 mg total daily dose.

In addition, the arsenic carrier could be delivered via charged and uncharged matrices used as drug delivery devices such as cellulose acetate membranes, also through targeted delivery systems such as fusogenic liposomes attached to antibodies or specific antigens.

In practical use, an arsenic compound can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, micro-crystalline cellulose, diluents, granulating agents, lubricants, binders, disintegrating agents, and the like in the case of oral solid preparations e.g., powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% w/v, normal saline or other solutions. The total dose of the arsenic compound may be administered in a vial of intravenous fluid, e.g, ranging from about 2 ml to about 2000 ml. The volume of dilution fluid will vary according the total dose administered.

Other embodiments of the invention will be apparent to those skilled in the art from consideration of the specification and practice of the invention disclosed herein.

EXAMPLES

Example 1

Use of Animal Models to Test Analgesic Activity

Animal models for chemical-induced pain were used to determine the analgesic activity of various concentrations of sodium meta arsenite and arsenic trioxide.

Mouse Formalin Test. Sodium meta arsenite or arsenic trioxide was administered orally (PO) or intraperitoneally (IP), respectively, to groups of ten CD-1 (Crl.) derived male mice weighing 24+/−2 g. Sodium meta arsenite and vehicle (distilled water) or arsenic trioxide and vehicle were each administered one hour before subplantar injection of formalin 0.02 ml, 2% solution). Reduction of the formalin-induced hind paw licking time recorded at five minute intervals during the following 0 to 35 minute period after formalin injection by 50% or more (≥50%) indicated significant analgesic activity. Statistical analysis was performed using One-way ANOVA followed by Dunnett's test for comparing results obtained with sodium meta arsenite or arsenic trioxide those Obtained With Vehicle (control) alone. Significance was considered at $P<0.05$. The results are summarized below:

| | | | Sodium Meta Arsenite | | | | | | |
|---|---|---|---|---|---|---|---|---|---|
| | | | Hind paw licking time (Seconds) (Mean ± SEM) | | | | | | |
| | | Dose | Time (minutes) | | | | | | |
| Treatment | Route | mg/kg | 0-5 | 5-10 | 10-15 | 15-20 | 20-25 | 25-30 | 30-35 |
| Vehicle | PO- | — | 66.7 ± 6.4 | 0.9 ± 0.9 | 10.1 ± 4.3 | 81.7 ± 20.7 | 72.4 ± 25.4 | 30.8 ± 10.1 | 4.8 ± 10.6 |
| SMA | PO | 10 | 51.2 ± 5.2 | 0.1 ± 0.1 | 4.7 ± 4.6 | 6.5* ± 4.5 | 20.5 ± 10.8 | 29.2 ± 7.6 | 6.6 ± 4.2 |

-continued

| | | | Sodium Meta Arsenite | | | | | | |
|---|---|---|---|---|---|---|---|---|---|
| | | Dose | Hind paw licking time (Seconds) (Mean ± SEM) Time (minutes) | | | | | | |
| Treatment | Route | mg/kg | 0-5 | 5-10 | 10-15 | 15-20 | 20-25 | 25-30 | 30-35 |
| SMA | PO | 1 | 54.9 ± 6.3 | 2.7 ± 1.8 | 7.6 ± 2.8 | 44.6 ± 13.5 | 55.7 ± 13.9 | 45.0 ± 19.3 | 21.3 ± 9.7 |
| SMA | PO | 0.1 | 76.1 ± 8.6 | 4.3 ± 4.2 | 24.0 ± 10.4 | 69.4 ± 13.0 | 46.0 ± 11.8 | 44.6 ± 13.0 | 4.9 ± 1.8 |
| Morphine | PO | 30 | 20.8 ± 3.6 | 0.1 ± 0.1 | 2.01.8 | 2.0* ± 2.0 | 10.4* ± 8.2 | 16.2 ± 8.4 | 3.3 ± 1.8 |

SMA: sodium meta arsenite
*P < 0.05 versus the vehicle control group

The results indicate that oral administration of sodium meta arsenite at 10 mg/kg caused significant analgesic activity at 15-20 minutes after formalin challenge. The standard, morphine, caused significant analgesic effect during the early (0-5 minutes) and late (15-25 minutes) phases after formalin injection, as expected.

| | | | Arsenic Trioxide | | | | | | |
|---|---|---|---|---|---|---|---|---|---|
| | | Dose | Hind paw licking time (Seconds) (Mean ± SEM) Time (minutes) | | | | | | |
| Treatment | Route | mg/kg | 0-5 | 5-10 | 10-15 | 15-20 | 20-25 | 25-30 | 30-35 |
| Vehicle | IP- | 5 ml/kg X | 78.9 | 8.5 | 40.5 | 58.7 | 78.8 | 61.3 | 20.7 |
| | | SEM | 6.8 | 2.7 | 10.5 | 18.8 | 15.0 | 20.2 | 12.4 |
| AT | IP | 10 mg/kg X | 9.0* | 0.3* | 0.0* | 0.0* | 0.0* | 0.0* | 0.0 |
| | | SEM | 6.3 | 0.3 | 0.0 | 0.0 | 0.0 | 0.0 | 0.0 |
| AT | IP | 1 mg/kg X | 74.6 | 2.6* | 15.6* | 40.0 | 57.1 | 53.5 | 30.0 |
| | | SEM | 11.3 | 1.5 | 5.5 | 13.3 | 18.1 | 15.3 | 18.8 |
| Morphine | IP | 10 mg/kg X | 29.7* | 0.0* | 0.7* | 3.3* | 22.8* | 30.1 | 40.8 |
| | | SEM | 5.2 | 0.0 | 0.7 | 1.7 | 13.8 | 6.4 | 11.5 |

AT: Arsenic Trioxide
*P < 0.05 versus the vehicle control group using one-way ANOVA followed by Dunnett's test Intraperitoneal injection of arsenic trioxide at 10 mg/kg caused significant inhibition of the licking response to formalin challenge at the intervals of 0-5, 5-10, 10-15, 15-20, 20-25 and 25-30 minutes after formalin challenge, whereas response to the lower dose of arsenic trioxide (1 mg/kg) was limited to the intervals of 5-10 and 10-15 minutes after challenge. Concurrently run standard morphine HCl was associated with analgesic effect at 0-25 minutes after formalin challenge.

Acetic Acid-Induced Pain Response Assay. Sodium meta arsenite was evaluated for possible analgesic activity in the mouse acetic acid-induced pain response assay. Sodium meta arsenite was administered orally at doses of 10, 1 and 0.1 mg/kg for possible analgesia in the mouse. Distilled water was used as vehicle. One hour before injection of acetic acid (0.5%, 20 ml/kg IP), sodium meta arsenite was administered orally to groups of 10 CD-1 derived male mice, weighing 24±2 g. Significant analgesic activity was defined as a reduction in number of writhing responses by 50% or more (≥50%) relative to control groups at 5-10 minutes after acetic acid administration.

Administration of 10 mg/kg sodium meta arsenite was associated with significant analgesic activity (average 7 writhing events versus 16 for control). At lower doses sodium meta arsenite had no analgesic effect.

Example 2

Use of Animal Models to Test Anti-Inflammatory Activity of Sodium Meta Arsenite and Arsenic trioxide Sodium meta arsenite and arsenic trioxide were tested for possible protective effects against lipopolysaccharide-induced septic shock in mice.

LPS-Induced Pro-inflammatory Cytokine Production. Sodium meta arsenite was administered orally at 0.1, 1 and 10 mg/kg doses, one hour prior to challenge with lipopolysaccharide (LPS; 30 mg/kg IP; *Escherechia coil* 055:B5). Two hours after LPS challenge, 0.1 ml blood samples were taken from the mice via the retro-orbital and centrifuged to yield plasma for cytokine measurements by Luminex. After blood collection, mortality was monitored and recorded every 12 hours over a 3-day period. Reduction in mortality by 50 percent or more (≥50%) indicates significant protection. The results are shown in the table below:

| Route | Dose | % Protection |
|---|---|---|
| Sodium Meta Arsenite: | | |
| PO | 10 mg/kg | 25 |
| PO | 1.0 mg/kg | 25 |
| PO | 0.1 mg/kg | 12 |

-continued

| Route | Dose | % Protection |
|---|---|---|
| Dexamehasone 21-acetate | | |
| PO | 3 mg/kg | (75) |

The results show that sodium meta arsenite at doses of 0.1, 1.0, and 10 mg/kg PO afforded moderate protection against LPS-induced septic shock in mice. A significant inhibition of IL-1β secretion at 1 and 10 mg/kg PO sodium meta arsenite and inhibition of IL-6 (versus dexamethasone at 3 mg/kg) at 10 mg/kg were also observed, Sodium meta arsenite had no effect on secretion of TNF-α, KC or MCP-1.

LPS-Induced Neutrophilia in Lung Tissue. Sodium meta arsenite was evaluated for possible protective activity in a mouse model of LPS-induced neutrophilia in lung tissues. Sodium meta arsenite at doses of 0.1, 1 and 10 mg/kg was administered orally (PO) two hours before challenge with LPS. Twenty-four hours after LPS challenge, branchoaveolar lavage fluid was harvested from individual animals for total and differential cell counts.

Sodium meta arsenite at 10 mg/kg PO was not associated with any significant changes in cell counts. However, at 1 mg/kg a significant decrease in white blood cell (total) and neutrophil (differential) and monocyte counts versus vehicle control treated with LPS were observed.

Dexamethasone at 1 mg/kg PO afforded significant protection in terms of suppression of total white blood cell, as well as differential neutrophil and monocyte counts relative to control.

At 10 mg/kg, but not 1 or 0.1° mg/kg, administration of sodium meta arsenite correlated with a significant suppression of TNF-α similar to dexamethasone, the standard. At 1 mg/kg, but not 0.1 mg/kg or 10 mg/kg, administration of sodium meta arsenite correlated with significant reduction in KC similar to dexamethasone. The KC effect did not appear to be dose-related. At no concentration of sodium meta arsenite was secretion of 1L-1β, Il-6 or MCP-1 observed in brachoaveolar lavage fluid.

Example 3

Immunosuppression Studies

Hyperplasia of popliteal lymph nodes (PLN) has been used as a dependable indicator of lymphatic system reaction in host-versus-graft studies. The heterotropic heart transplantation model in the rat has been used successfully to evaluate immunosuppressive agents. A combination of PLN hyperplasia assay and heart transplantation model was used to obtain information relating to the efficacy of host lymphocytes in both alloreactive proliferation and allorejection. The results show that sodium meta arsenite has immunosuppressive effects.

Heart Transplantation. Donor hearts were transplanted into the recipient mouse as described (Chen et al., Transplantation, 56:661-666, 1993; Chen et al., The Journal of Immunology, 152:3107-3318, 1994). The transplanted donor hearts were checked every day and sodium meta arsenite was administered for two weeks or until the graft was rejected, whichever occurred first.

In the heart transplantation model, the higher dose (10 mg/kg) sodium meta arsenite showed a slight immunosuppressive effect in animals treated with alloantigen and an overall positive effect on the transplant. It appears that sodium meta arsenite may compromise the reaction of host lymphocytes to alloantigen at the higher dose. Thus, the arsenic compounds of the invention are also immunosuppressive agents.

Example 4

Type-II Collagen Induced Arthritis

Rat collagen arthritis is an experimental model of polyarthritis that has been widely used for preclinical testing of numerous anti-arthritic agents that are either under preclinical or clinical investigation or are currently used as therapeutics in this disease. The hallmarks of this model are reliable onset and progression of robust, easily measurable, polyarticular inflammation, marked cartilage destruction with pannus formation and mild to moderate bone resorption and periosteal bone proliferation. Therapeutic agents that inhibit Il-1 production or activity are especially active in this test system, but other types of anti-inflammatory agents have good to excellent activity.

This study was undertaken to determine the dose responsive oral (PO) efficacy of sodium meta arsenite and intraperitoneal (IP) efficacy of arsenic trioxide, respectively, administered daily for inhibition of the inflammation (paw swelling), cartilage destruction and bone resorption that occurs in developing type II collagen arthritis in rats.

Animals (8 per group, 4 per group for normals) were anesthesized with Isoflurane and injected with 300 µl Freund's incomplete adjuvant (Difco, Detroit, Mich.) containing 2 mg/mL bovine type II collagen. (Elastin products, Owensville, Mo.) at the base of the tail and two sites on the back on days 0 and 6. Dosing by IP or oral route (QD at 24 hour intervals) was initiated on day 0 of the study and continued through day 16. Experimental groups were as follows:

| Sodium Meta Arsenite: | | |
|---|---|---|
| Group | N | Treatment: Oral, QD days 0-16, 5 ml/kg |
| 1 | 4 | Normal controls plus water |
| 2 | 10 | Arthritis plus water |
| 3 | 10 | Arthritis plus sodium meta arsenite 10 mg/kg |
| 4 | 10 | Arthritis plus sodium meta arsenite 5 mg/kg |
| 5 | 10 | Arthritis plus sodium meta arsenite 0.1 mg/kg |
| 6 | 10 | Arthritis plus MTX 0.075 mg/kg |

| Arsenic Trioxide: | | |
|---|---|---|
| Group | N | QD Treatment day 0-16, 10 ml/kg IP groups 1-4 |
| 1 | 4 | Normal controls plus vehicle IP |
| 2 | 8 | Arthritis plus vehicle |
| 3 | 8 | Arthritis plus arsenic trioxide 10 mg/kg IP |
| 4 | 8 | Arthritis plus arsenic trioxide 1 mg/kg IP |
| 5 | 8 | Arthritis plus arsenic trioxide 10 mg/kg PO (5 ml/kg) |

Rats were weighed on days 0, 3, 6, 9-17 of the study and caliper measurements of ankles were taken every day beginning on day 9 (or day 0 of arthritis). After final body weight measurement on day 17, animals were anesthesized for serum and then euthanized for tissue collection. Hind paws were transected at the level of the medial and lateral malleolus, weighed and placed in formalin, with knees, for microsopy. Liver, spleen and thymus were removed from each animal, weighed and discarded.

A PK sampling was done on days 16 using 6 animals per group (arthritic) as follows: animals 1, 2, 3 were bled for pre-dose, 2 and 8 hour samples; animals 6, 7 and 8 were bled for 1, 4 and 12 hour post-dose samples.

Morphologic pathology of the sodium meta arsenite-treated rats was undertaken, but none was conducted for the arsenic trioxide-treated-animals. For these tests, preserved and decalcified ankle and knee joints were cut in half longitudinally (ankles) or in the frontal plane (knees), processed through graded alcohols and a clearing agent, infiltrated and embedded in paraffin, sectioned and stained with Toluidine Blue. All tissues were examined microscopically by a board certified veterinary pathologist.

Collagen arthritic ankles and knees were given scores of 0-5 (0=normal; 5=severe) for inflammation, pannus formation and bone resorption. Statistical analysis of body/paw weights, paw AUC (area under the curve) parameters were evaluated using a Student's t-test with significance set at the 5% significance level.

Percent inhibition of paw weight and AUC was calculated using the following formula:

% inhibition=$A-B/A \times 100$

A=Mean Disease Control−Mean Normal
B=Mean Treated−Mean Normal

Results: Sodium Meta Arsenite: Body weight loss (due to arthritis) was significantly inhibited by treatment with 10 mg/kg sodium meta arsenite (100% inhibition), or MTX (96%), as compared to vehicle treated disease control rats. Calculated $ED_{50}$ value=1.929 mg/kg.

Significant inhibition of ankle diameter was seen in rats treated with 10 mg/kg sodium meta arsenite (days 9, 11-17) or MTX (days 10-17).

Inhibition of ankle diameter (AUC) was significant for rats treated with 10 mg/kg sodium meta arsenite (73% inhibition), or MTX (97%), as compared to disease controls. Calculated $ED_{50}$ value=8.499 mg/kg.

Inhibition of final paw weight was significant for rats treated with 10 mg/kg sodium meta arsenite (83%), or MTX (95%), as compared to disease controls. Calculated $ED_{50}$ value=7.116 mg/kg.

Relative liver weights were increased, above normal and arthritic controls for rats treated with 10 mg/kg sodium meta arsenite (17% increase over disease controls).

Relative spleen weights were reduced by treatment with 10 mg/kg sodium meta arsenite (10%), or MTX (10%), as compared to disease control rats. Relative thymus weights were significantly reduced in rats treated with 1 mg/kg sodium meta arsenite (20%), as compared to disease controls.

All vehicle treated disease control rats had marked to severe synivitis and periarticular inflammation in at least one, and usually both, ankle joints with minimal to moderate pannus and bone resorption, and minimal to marked cartilage damage. In contrast, all ankle histopathology parameters were significantly inhibited to normal in rats treated with 10 mg/kg sodium meta arsenite (85%) inhibition, or MTX (97%). Calculated $ED_{50}$ value=7.080 mg/kg.

All ten vehicle treated disease control rats had moderate to severe synovitis and periarticular inflammation in at least one knee joint with minimal to moderate pannus and bone resorption, and cartilage damage. In contrast-knee histopathological parameters were significantly inhibited toward normal in rats treated with 10 mg/kg sodium meta arsenite (87% inhibition), or MTX (100%). Calculated $ED_{50}$ value=7.924 mg/kg.

The results obtained from this study indicate that oral, daily treatment of rats with 10 mg/kg sodium meta arsenite effectively inhibits the clinical and histopathological changes associated with developing type II collagen arthritis.

Results: Arsenic Trioxide and Sodium Meta Arsenite: Body weight loss was significantly inhibited by IP, QD treatment with 10 mg/kg arsenic trioxide (55% inhibition), or PO, QD treatement with 10 mg/kg sodium meta arsenite (85%), as compared to vehicle treated disease control rats.

Significant inhibition of decrease in ankle diameter was seen in rats treated with 10 mg/kg arsenic trioxide (days 10-17), or 10 mg/kg sodium meta arsenite (days 11-17). Inhibition of ankle diameter AUC was significant for rats treated IP, QD with 10 mg/kg arsenic trioxide (80% inhibition); and PO, QD with 10 mg/kg sodium meta arsenite (66%), as compared to disease controls.

Inhibition of final paw weight was significant for rats treated IP, QD with 10 mg/kg arsenic trioxide (71% inhibition), or PO, QD with 10 mg/kg sodium meta arsenite (69%), as compared to disease controls.

Relative liver weights were increased above arthritic controls for rats treated with 1 or 10 mg/kg arsenic trioxide (6% and 10%, respectively), or 10 mg/kg sodium meta arsenite (14%).

Relative spleen weights were reduced, below normal and arthritic controls, by treatment with 10 mg/kg arsenic trioxide (21%) or 10 mg/kg sodium meta arsenite (10%), as compared to disease control rats. Relative thymus weights were reduced below arthritic controls in rats treated with 10 mg/.kg arsenic trioxide.

The results of this study indicate that intraperitoneal, daily treatment of rats with 10 mg/kg arsenic trioxide, or oral, daily treatment with 10 mg/kg sodium meta arsenite effectively inhibits clinical changes associate with developing type II collagen arthritis.

Example 5

Adjuvant Induced Arthritis

This study was undertaken to evaluate the efficacy of sodium meta arsenite (PO, QD days 0-13) in inhibiting periarticular inflammation and bone resorption of established adjuvant arthritis. Rat adjuvant arthritis is an experimental model of polyarthritis that has been widely used for preclinical testing of numerous anti-arthritic agents. The hallmarks of this model are reliable onset and progression of robust, easily measurable, polyarticular inflammation, marked bone resorption and periosteal bone proliferation. Cartilage destruction occurs, but is disproportionately mild in comparison to the inflammation and bone destruction that occurs. Use of the adjuvant model provides an opportunity to study pathologic changes in a variety of tissues other than the joints.

Animals were randomly assigned to groups (8 per group for adjuvant, 4 per group for normal controls) and anesthesized with Isoflurane and injected with 100 μlFreund's complete Adjuvant (Sigma, st. Louis, Mo.) containing lipoidal amine (60 mg/ml) at the base of the tail on day 0. Dosing by the PO route was initiated on day 0 (prophylactic treatment) with vehicle (water), sodium meta arsenite (3, 10, or 30 mg/kg) or methotrexate (MTX) (0.1 mg/kg). Treatment continued until day 13. Experimental groups were as follows:

| Group | N | Treatment: PO, QD days 0-13, |
|---|---|---|
| 1 | 4 | Normal controls plus water |
| 2 | 8 | Adjuvant plus water |
| 3 | 8 | Adjuvant plus sodium meta arsenite 30 mg/kg |
| 4 | 8 | Adjuvant plus sodium meta arsenite 10 mg/kg |
| 5 | 8 | Adjuvant plus sodium meta arsenite 3 mg/kg |
| 6 | 8 | Adjuvant plus MTX 0.1 mg/kg |

Rats were weighed on days 0, 4 and 8-13 at which times dose volumes were adjusted. On day 7 (prior to swelling onset, but after establishment of systemic disease), caliper measurements were made of ankle joints. Ankles were measured again on days 8-14. Final body weights were taken on day 14. On day 14, animals were euthanized and hind paws, liver and spleen were removed and weighed. Paws and spleen were placed in formalin and processed for H&E and microscopy.

Adjuvant arthritic ankles (right only) were given scores of 0-5 (0=normal; 5=severe) for inflammation and bone resorption. Statistical analysis of ankle joint diameter was analyzed by determining the area under the dosing curve (AUC). For calculation of AUC, the daily measurement of ankle joints (using a caliper) for each rat were entered into Microsoft Excel where the area between the treatment days after the onset of disease to the termination day was computed. Means for each group wree determined and % inhibition for arthritis controls was calculated by comparing values for treated and normal animals. Paw weights, spleen and liver weights and histology parameters (mean±SE) for each group were analyzed for differences using the Student's t test or other appropriate analysis as determined after seeing the data. In both cases, significance was set at $p \leq 0.05$.

Percent inhibition of paw weight and AUC was calculated using the following formula:

$$\% \text{ inhibition} = A - B/A \times 100$$

A=Mean Disease Control−Mean Normal
B=Mean Treated−Mean Nbrmal $ED_{50}$ calculations were done by plotting th % inhibition versus the natural log of the dose concentration and generating a sigmoidal dose-response curve (variable slope). The zero concentration dose (vehicle group) was incorporated into the graph by assigning it a dose value of 2 log units lower than the lowest dose given. Constraints of the curve were set at 0 and 100%. Software was used to generate an equation for the curve and calculated the concentration at which animals would show 50% inhibition of the parameter ($ED_{50}$).

Results. Mean body weight decrease over time (due to arthritis) was inhibited in rats treated PO with 0.1 mg/kg MTX (significant days 10-14), as compared to vehicle treated control rats. Mean body weight loss over time was significantly increased in rats treated with 30 mg/kg sodium meta arsenite (days 4, 8, 9), as compared to the vehicle controls.

Inhibition of body weight loss from day zero was significant for rats treated with 0.1 mg/kg MTX (91% inhibition). Body weight loss from day 0 was non-significantly (2-14%) inhibited by treatment with sodium meta arsenite (3, 10 and 30 mg/kg), as compared to the vehicle controls.

Significant inhibition of ankle diameter increase was observed in rats treated PO with 3 mg/kg sodium meta arsenite (significant day 9), 10 mg/kg sodium meta arsenite (significant days 8-14), 30 mg/kg sodium meta arsenite (significant days 8-14), and 0.1 mg/kg MTX (significant days 8-14), as compared to vehicle controls.

Significant and dose responsive inhibition of ankle diameter AUC increase was observed in rats treated PO with 10 mg/kg sodium meta arsenite (46% inhibition), 30 mg/kg sodium meta arsenite (83% inhibition) and 0.1 mg/kg MTX (96% inhibition), as compared to vehicle controls. Calculated $ED_{50}$ for sodium meta arsenite=10.62 mg/kg.

Final paw weight increase due to arthritis was significantly and dose-responsively inhibited in animals treated PO with 10 mg/kg sodium meta arsenite (28% inhibition), 30 mg/kg sodium meta arsenite (83% inhibition), and 0.1 mg/kg MTX (99% inhibition), as compared to vehicle controls. Calculated $ED_{50}$ for sodium meta arsenite=1421 mg/kg.

Relative spleen weights (increased due to inflammation and enhanced extramedullary hemtopoiesis) were significantly and dose-responsively reduced toward normal in rats treated PO with 10 mg/kg sodium meta arsenite (50% reduction), 30 mg/kg sodium meta arsenite (91% reduction), and 0.01 MT (77% reduction), as compared to vehicle controls.

Relative liver weights were significantly reduced toward normal in rats treated with MTX (100% reduction). Relative liver weights were non-significantly reduced (7-29%) by treatment with sodium meta arsenite (3, 10 and 30 mg/kg).

Histopathologic bone resorption was significantly and dose-responsively inhibited in rats treated PO with 10 mg/kg sodium meta arsenite (59% inhibition), 30 mg/kg sodium meta arsenite (81% inhibition), and 0.1 mg/kg MTX (100% inhibition), as compared to vehicle controls. Calculated $ED_{50}$ for sodium meta arsenite=9.243 mg/kg.

Significant and dose-responsive inhibition of histopathologic inflammation as compared to the vehicle controls was observed in rats treated PO with 10 mg/kg sodium meta arsenite (24% inhibition), 30 gm/kg sodium meta arsenite (76% inhibition) and 0.1 mg/kg MTX (99% inhibition). Calculated $ED_{50}$ for sodium meta arsenite=17.25 mg/kg.

Ankle measurements (dorsal to ventral) were significantly and dose-responsively inhibited by treatment with 10 mg/kg sodium meta arsenite (36% inhibition), 30 mg/kg sodium meta arsenite (81% inhibition) and 0.1 mg/kg MTX (97% inhibition), as compared to vehicle controls. Calculated $ED_{50}$ for sodium meta arsenite=13.65 mg/kg.

Splenic inflammation and lymphoid atrophy were significantly and dose-responsively inhibited in rats receiving 10/kg sodium meta arsenite (32% and 29% inhibition, respectively), 30 mg/kg sodium meta arsenite (89% and 39% inhibition, respectively) and 0.1 mg/kg MTX (100% and 50% inhibition, respectively), as compared to vehicle controls.

Results of this study indicate that oral (PO) treatment with 10 mg/kg (OD), or 30 mg/kg (QD2) sodium meta arsenite effectively and dose-responsively inhibits the clinical and histopathological changes associated with developing adjuvant arthritis. A daily dose of 30 mg/kg sodium meta arsenite was toxic (based on body weight changes), but every other dat dosing during the active phase of the disease was well tolerated and body weights then tracked with disease controls from day 10 to study termination.

Example 6

Treatment of Tumor Induced Osteolysis With Sodium Meta Arsenite

In this study, a candidate therapy for treatment of tumor-induced bone osteolysis, sodium meta arsenite, was evaluated using a syngeneic rat model of bone cancer. In brief, the rat mammary gland carcinoma cell line, MRMT-1, was injected into the marrow space of the proximal tibia on Day 1 and the animals were dosed by oral gavage with vehicle sodium meta arsenite once daily from Days 1-14. Morphine was used as a reference article and was dosed just prior to behavioral testing. At the conclusion of the experimental period, the left tibiae were excised for radiographic confirmation of tumor osteolysis. Radiographs were used to select two representative bones from each group for micro-CT scanning. All bone samples were decalcified for TRAP staining and evaluation of osteoclastic activity (resorbing surfaces) and for histopathological assessment of bone structure and tumor burden. Sodium meta arsenite efficacy was based on a comparison with the tumor-inoculated, vehicle-treated group.

Figure 1:
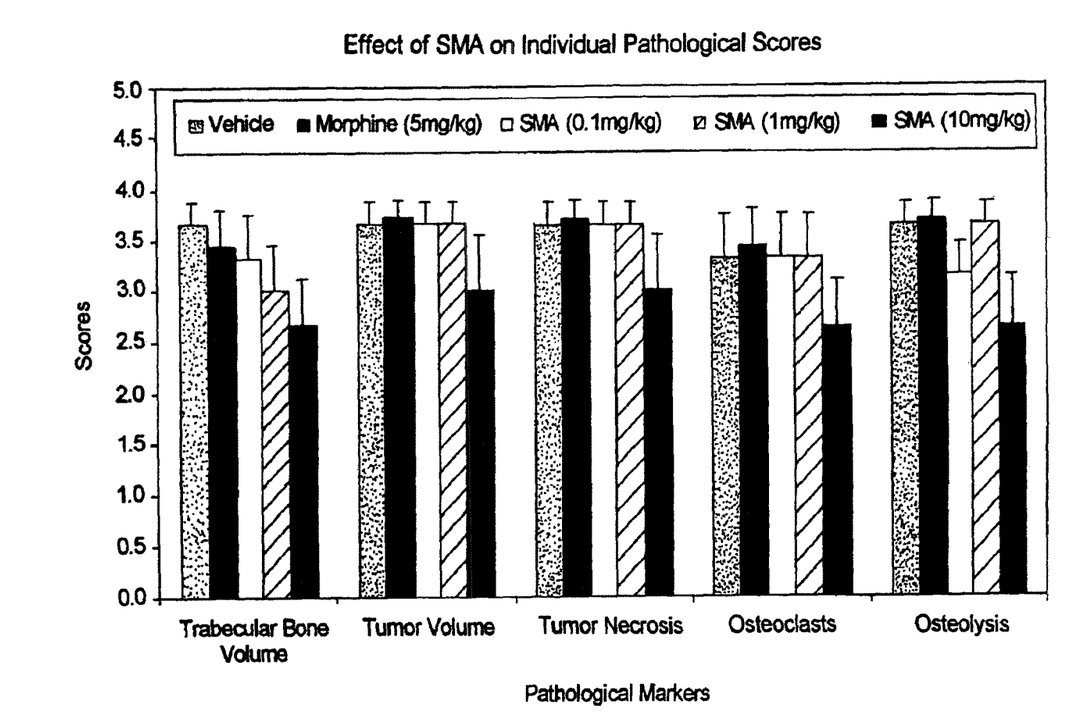
FIG. 1 is a bar graph of data obtained through histopathological assessment of bone necrosis and inflammation caused by tumor burden in rats treated with sodium meta arsenite.

The histopathological results showed that at the dose level of 10 mg/kg sodium meta arsenite demonstrated a positive trend on improving the various aspects of cancer-induced bone damage. The data show that at 10 mg/kg sodium meta arsenite had a strong positive trend toward ameliorating tumor-induced osteoclasts and osteolysis. The data are shown in FIG. 1.

Example 7

Pharmakokinetic Profile of Sodium Meta Arsenite Following Oral and I.V Administration Plasma and brain pharmacokinetic profiles following oral (PO) and intravenous (IV) administration of sodium meta arsenite in male CD-1 mice were determined. Seventy three male CD-1 (ICR) albino mice (approximately four weeks old, 18-27 g upon start of testing) were randomly assigned to treatment gropus. Animals were fasted for two hours prior to administration of test drug. The animals were treated with 10 mg/kg (PO) or 5 mg/kg (IV), with a target dose volume of 10 mUkg. Following administration, blood samples (0.2 to 0.3 were obtained via the vena cava under isolurane anesthesia at 5, 15, 30, 60, 120, 240, 480, 14490, 1920, 2880, 3360, and 4320 minutes post-dose. Immediately following each blood collection, the animals were sacrificed and the brain collected at 5, 30, 60, 120, 240, 480, 1440, 2880 and 4320 minutes post-dose.

The plasma and whole brain samples were digested with concentrated nitric acid in a Teflon bomb at 105° C. The digestate was diluted to 40 mL for analysis by ICP-MS. The digestate was aspirated into the inductively coupled Plasma and the resulting ions were extracted by a vacuum interface into a quadrapole mass analyzer. The amount of arsenic in the samples was measured by comparison t response at a standard solution of mass 75. NRCC-DOLT-3 and DORM-2 were analyzed as standard reference materials.

The study sample concentration versus data was analyzed to generate the following PK parameters by noncompartmental analysis (WinNonlin, version 2.1):

| Parameter | Units | Notes |
|---|---|---|
| $T_{max}$ | Hour | Time to reach maximum concentration |
| $C_{max}$ | Ng/mL | Highest concentration within the timeframe |
| $AUC_{all}$ | Ng · hr/mL | Area under the curve, generated by log-linear trapezoidal method for interpolation |
| F % | % | Bioavailability of orally dosed animals |

The results are set forth in the tables below:

| Plasma PK Results: Sodium Meta Arsenite (PO, 10 mg/kg) | | |
|---|---|---|
| Pharmacokinetic (PK) Parameter | Units | PK Results (N = 3) |
| $AUC_{all}$ | mg * hr/Kg | 6.85 |
| $C_{max}$ | Mg/Kg | 0.52 |
| $T_{max}$ | Hr | 4 |
| F % | % | 101% |

Pharmacokinetic analysis completed using the mean (N = 3) concentration value at each collection timepoint.

| Plasma PK Results: Sodium Meta Arsenite (IV, 5 mg/kg) | | |
|---|---|---|
| Pharmacokinetic (PK) Parameter | Units | PK Results (N = 3) |
| $AUC_{all}$ | mg * hr/Kg | 3.38 |
| $C_{max}$ | Mg/Kg | 0.41 |
| $T_{max}$ | Hr | 0.25 |
| F % | % | N/A |

Pharmacokinetic analysis completed using the mean (N = 3) concentration value at each collection timepoint.
N/A: Not applicable

| Brain PK Results: Sodium Meta Arsenite (PO, 10 mg/kg) | | |
|---|---|---|
| Pharmacokinetic (PK) Parameter | Units | PK Results (N = 3) |
| $AUC_{all}$ | mg * hr/Kg | 6.73 |
| $C_{max}$ | Mg/Kg | 0.33 |
| $T_{max}$ | Hr | 8 |
| F % | % | 87% |

Pharmacokinetic analysis completed using the mean (N = 3) concentration value at each collection time point.

| Brain PK Results: Sodium Met\a Arsenite (IV 5 mg/kg) | | |
|---|---|---|
| Pharmacokinetic (PK) Parameter | Units | PK Results (N = 3) |
| $AUC_{all}$ | mg * hr/Kg | 3.86 |
| $C_{max}$ | Mg/Kg | 0.32 |
| $T_{max}$ | Hr | 4 |
| F % | % | N/A |

Pharmacokinetic analysis completed using the mean (N = 3) concentration value at each collection timepoint.
N/A: Not applicable

What is claimed is:

1. A method of treating non-cancer associated inflammation in a mammal comprising orally administering to the mammal a therapeutically effective amount of a composition comprising sodium meta arsenite, wherein the non-cancer-associated inflammation is associated with a condition selected from the group consisting of lupus, asthma, pulmonary disease, autoimmune disease, immunological disorders, arthritis, multiple sclerosis, Crohn's disease, ulcerative colitis, stomach disorder, Herpes neuralgia and diabetes type I.

2. The method of claim 1 wherein the inflammation is associated with lupus.

3. The method of claim 1 wherein the inflammation is associated with diabetes type I.

4. The method of claim 1 wherein inflammatory pain is associated with the non-cancerous associated inflammation.

5. The method of claim 4 wherein the inflammatory pain is chronic pain.

6. The method of claim 4 wherein the inflammatory pain is caused by diabetic neuropathy.

7. The method of claim 1 wherein the inflammation is associated with diabetic vasculopathy, diabetic retinopathy or diabetic symptoms associated with insulitis.

8. The method of claim 7 wherein the inflammation is associated with diabetic vasculopathy.

9. The method of claim 7 wherein the inflammation is associated with diabetic symptoms of insulitis.

10. The method of claim 7 wherein the inflammation is associated with diabetic retinopathy.

\* \* \* \* \*